US006818671B1

(12) United States Patent
Embil et al.

(10) Patent No.: US 6,818,671 B1
(45) Date of Patent: Nov. 16, 2004

(54) NIMESULIDE CONTAINING TOPICAL PHARMACEUTICAL COMPOSITIONS

(76) Inventors: Koral Embil, Olfahane Sokok No: 40, Bomonti, Sisli 80630, Istanbul (TR); Ray Figueroa, 8424 NW. South River Dr., Medley, FL (US) 33166

( * ) Notice: Subject to any disclaimer, the term of this patent is extended or adjusted under 35 U.S.C. 154(b) by 0 days.

(21) Appl. No.: 09/762,630

(22) PCT Filed: Aug. 12, 1999

(86) PCT No.: PCT/IB99/01460

§ 371 (c)(1), (2), (4) Date: Apr. 10, 2001

(87) PCT Pub. No.: WO00/09117

PCT Pub. Date: Feb. 24, 2000

(30) Foreign Application Priority Data

Aug. 12, 1998 (GB) ............................................ 9817573

(51) Int. Cl.[7] ................................................ A61K 31/18

(52) U.S. Cl. ....................................... 514/605; 514/601

(58) Field of Search ................................. 514/605, 601

(56) References Cited

U.S. PATENT DOCUMENTS

| | | | | |
|---|---|---|---|---|
| 3,840,597 A | | 10/1974 | Moore et al. | |
| 5,716,609 A | | 2/1998 | Jain et al. | |
| 5,744,458 A | * | 4/1998 | Kruse et al. | 514/91 |

FOREIGN PATENT DOCUMENTS

| | | | | |
|---|---|---|---|---|
| EP | 0782855 A | | 7/1997 | |
| EP | 0 782 855 | | 7/1997 | |
| EP | 0812587 A | | 12/1997 | |
| EP | 0 812 587 | | 12/1997 | |
| EP | 812587 A1 | * | 12/1997 | A61K/9/20 |
| EP | 0 812 591 | | 12/1997 | |
| EP | 0812591 A | | 12/1997 | |

* cited by examiner

*Primary Examiner*—Dwayne Jones
(74) *Attorney, Agent, or Firm*—Kilpatrick Stockton LLP

(57) ABSTRACT

This invention relates to compositions of nimesulide for topical application.

20 Claims, No Drawings

NIMESULIDE CONTAINING TOPICAL PHARMACEUTICAL COMPOSITIONS

TECHNICAL AREA

This invention relates to compositions of nimesulide for topical application.

BACKGROUND OF THE INVENTION

Nimesulide is a nonsteroidal anti-inflammatory agent (NSAID), which has poor solubility, especially in water. It has been formulated at various concentrations as a suspension in vehicles containing pharmaceutically acceptable excipients. These vehicles typically consist of aqueous gels containing about 1% nimesulide. Nimesulide in suspension may have limited therapeutic activity, as its percutaneous absorption is impaired by the difficulty of releasing free drug molecules from the suspensoid. Solubilised nimesulide, on the other hand, may offer the advantage of immediate availability of free drug molecules to the receptor site, and gels comprising solubilised nimesulide have been prepared using different pharmaceutical solvents. However, when the gel products comprising solubilised nimesulide are applied topically, they produce an unpleasant yellowish stain on the skin and/or clothing.

Many attempts have been made to provide nimesulide compositions of various kinds. They include those described in EP-A-0782855 and EP-A-0812587. In EP-A-0782855 particles of nimesulide are dispersed (not dissolved) in a base component. In EP-A-0812587, nimesulide is incorporated in a medium vaguely described as a "percutaneous absorption enhancing vehicle base", which comprises water as an essential ingredient and a surfactant such as glyceryl monoolein in an amount of up to 12% w/w.

SUMMARY OF THE INVENTION

Accordingly, it is an objective of the present invention to provide nimesulide compositions, which are both therapeutically effective and non-staining or substantially non-staining when applied topically. It has been found that this desirable combination of properties is achieved in the compositions of the present invention. The compositions of the present invention may enable the nimesulide to penetrate the upper layer of the skin (stratum corneum) rapidly. Once within the stat corneum, the nimesulide may be released into the deeper layers of the skin more slowly, which is advantageous in the treatment of the conditions for which nimesulide is used.

DETAILED DESCRIPTION OF THE INVENTION

The invention provides a composition for topical application comprising nimesulide in a glyceryl monoolein-solvent phase comprising glyceryl monoolein in an amount of 17–59% by weight of the composition.

The invention further provides a composition for topical application comprising nimesulide in a glyceryl monoolein-solvent phase, wherein the glyceryl monoolein-solvent phase may have a liquid crystal structure.

The invention further provides a composition for topical application comprising nimesulide, glyceryl monoolein and a non-aqueous solvent. Optionally the composition may also comprise a gelling agent, water and other additives.

The nimesulide is preferably used in the composition in an amount of 0.1–5% by weight, more preferably in an amount of 0.1–3% by weight, most preferably in an amount of around 1% by weight of the composition.

The glyceryl monoolein (or monooleate) may be used in an amount as low as 10–45% by weight, preferably in an amount of 17–45% by weight, more preferably in an amount of 17–59% by weight of the composition. Glyceryl monoolein is available commercially as a distilled monoglyceride mixture with a high monoolein content (for example "GMOrphic" from Eastman Chemicals, USA, or "Glycerol Monooleate" from an alternative manufacturer).

The non-aqueous solvent is preferably used in an amount of 40–82% by weight, more preferably 60–82% by weight of the composition. The solvent should be pharmaceutically acceptable and may for example be a $C_{1-6}$ alcohol, N-methylpyrrolidone, a glycol or an ether glycol (e.g. a $C_{2-6}$ compound such as propylene glycol, 1,3-butylene glycol, dipropylene glycol or diethylene glycol), an ether (e.g. a $C_{2-6}$ ether such as diethyl ether or diethylene glycol monoethyl ether (DGME)), or a $C_{8-22}$ glyceride or ethoxylated glyceride (e.g. capric, caprylic, arachinoic and behanoic glycerides and ethoxylated derivatives thereof, particularly caprylic/capric triglycerides or derivatives containing for example 6 polyoxyethylene units). Mixtures of these solvents can also be used. Preferably a solvent system containing DGME and a $C_{1-6}$ alcohol such as ethanol is used, preferably with the DGME in an amount of 35–45% by weight and the alcohol in an amount of 25–35% by weight of the composition. More preferably DGME is used on its own as solvent, preferably in an amount of 40–82% by weight, more preferably in an amount of 60–82% by weight of the composition.

The composition may also optionally include a gelling agent such as hydroxypropylcellulose or a fumed silicon dioxide (e.g. Cab-O-Sil). Preferably hydroxypropylcellulose is used. Although gelling agents are not required, they may assist in maintaining the long-term structural integrity and can influence the shelf life stability of a finished product. Gelling agents can additionally offer greater flexibility to the formulator in designing finished products with varied consistence and levels of thickness. Preferably gelling agents are used in an amount of 0.1–10% by weight, more preferably in an amount of 0.5–3% by weight of the composition.

The composition need not contain any water. However, it may optionally include water, preferably in amount of up to 15% by weight (for example 5–15% by weight), more preferably in an amount of up to 10% by weight of the composition.

Other ingredients may also optionally be included in the composition, for example capsicum oleoresin, capsaicin, nicotinates, camphor, menthol, turpentine oil, preservatives (e.g. propylparaben), antioxidants (e.g. BHT or BHA), sequestrant agents (e.g. EDTA) or colorants (e.g. FD&C Blue 1 or Yellow #5). Preferably such optional additives are included in an amount of up to 0.25% by weight, for example 0.001–0.25% by weight of the composition.

Preferably, the composition is in the form of a gel, solution, ointment or spray. Most preferably the composition is in the form of a gel. A gel is easy to apply—it does not drip like a solution may, and the dosage of a gel is usually more easily controlled than that of a spray. The gel may be a jelly-like material, for example formed from a nimesulide solution by the addition of a gelling agent. A nimesulide spray may be a nimesulide solution in a spraying device.

The nimesulide compositions can be used for a variety of indications characterised by pain and inflammation, or stiffness. Such indications are: osteoarthritis of superficial joints, such as the knee, ankle, wrist and elbow; rheumatism; acute musculoskeletal injuries and/or bruising; muscular cramp; strains; sprains; periarthritis; epicondylitis; tendinitis; bursitis; tenosynovitis; tennis elbow; back strain; lumbago; sciatica; neuralgia; and fibrositis.

The compositions may be prepared by first dissolving the nimesulide in the non-aqueous solvent(s) to form a solution. This solution may be heated to 30–90° C. and mixed with glyceryl monoolein, which may have previously been heated to 35–55° C. This mixing step may be followed by agitation and cooling to room temperature to form a clear nimesulide solution.

This clear nimesulide solution may alternatively be prepared by first dissolving glyceryl monoolein in the non-aqueous solvent(s) to form a solution. This solution may be heated to 30–90° C. and mixed with nimesulide, followed by agitation and cooling to room temperature to form a clear nimesulide solution.

Optionally, a gelling agent may be mixed into the nimesulide solution, either on its own or as a gel prepared with the non-aqueous solvent(s). If water and other optional additives are included in the composition, these may be mixed into the composition as a final step.

The present invention makes it possible to provide compositions, which have the advantage that they do not leave yellow stains on the skin and clothing upon application. It is believed that the nimesulide compositions of the present invention may be in the form of a liquid crystal structure.

The compositions are applied topically to the skin, which should be clean and is preferably cleansed before use. Cleaning provides a better surface for penetration by the composition, thus assisting in avoiding staining, and prevents surface materials such as salt or grime from complexing with any gelling agent present and coagulating the composition.

The following examples illustrate the invention.

EXAMPLE 1

| | |
|---|---|
| Diethylene glycol monoethyl ether (DGME) | 42.5% w/w |
| SD alcohol (ethanol) | 30% w/w |
| Water | 10% w/w |
| Nimesulide | 1% w/w |
| Glyceryl monoolein | 16.5% w/w |

The nimesulide was dissolved in DGME and ethanol to form a solution, which was heated to 45° C. This heated solution was added to glyceryl monoolein, which had previously been heated to 45° C. The mixture was agitated and cooled to room temperature to give a clear solution, to which water was added.

EXAMPLE 2

| | |
|---|---|
| Diethylene glycol monoethyl ether (DGME) | 40% w/w |
| SD alcohol (ethanol) | 25.5% w/w |
| Water | 10% w/w |
| Fumed silicon dioxide | 7% w/w |
| Nimesulide | 1% w/w |
| Glyceryl monoolein | 16.5% w/w |

The nimesulide was dissolved in DGME and ethanol to form a solution, which was heated to 45° C. This heated solution was added to glyceryl monoolein, which had previously been heated to 45° C. The mixture was agitated and cooled to room temperature to give a clear solution. The gelling agent (silicon dioxide) was then mixed into the solution to the desired consistency to provide a clear gel. Finally water was mixed into the gel.

Alternatively, the nimesulide was added slowly to DGME at 48–50° C. to form a solution. Glyceryl monoolein was heated to 48–50° C. and added slowly to the nimesulide solution with mixing to give a clear nimesulide solution, which was cooled to room temperature. Ethanol and gelling agent were mixed thoroughly to form an alcoholic gel, which was mixed slowly into the nimesulide solution at room temperature to give a clear gel. Finally water was mixed into the gel.

EXAMPLE 3

| | |
|---|---|
| Diethylene glycol monoethyl ether (DGME) | 42.5% w/w |
| SD alcohol | 30% w/w |
| Water | 10% w/w |
| Nimesulide | 1% w/w |
| Glyceryl monoolein | 16.475% w/w |
| Capsaicin | 0.025% w/w |

A clear gel was prepared as described in Example 1. The capsaicin was then added in a final step and mixed into the gel until dissolved and homogenous.

EXAMPLE 4

| | |
|---|---|
| Diethylene glycol monoethyl ether (DGME) | 81% w/w |
| Hydroxypropylcellulose | 1% w/w |
| Nimesulide | 1% w/w |
| Glyceryl monoolein | 17% w/w |

The nimesulide was dissolved in DGME to form a clear solution, which was heated to 43–47° C. Glyceryl monoolein was heated to 43–47° C. and mixed into the solution to form a clear solution, which was mixed and cooled to room temperature. The mixing speed was increased enough to create a vortex of mixing, and hydroxypropylcellulose was added. The mixing was continued until a clear gel was obtained.

EXAMPLE 5

| | |
|---|---|
| Diethylene glycol monoethyl ether (DGME) | 63.1% w/w |
| Hydroxypropylcellulose | 1.4% w/w |
| Nimesulide | 1% w/w |
| Glyceryl monoolein | 34.5% w/w |

A gel was obtained using the method described in Example 5.

EXAMPLE 6

| | |
|---|---|
| Diethylene glycol monoethyl ether (DGME) | 82% w/w |
| Nimesulide | 1% w/w |
| Glyceryl monoolein | 17% w/w |

The nimesulide was dissolved in DGME to form a clear solution, which was heated to 43–47° C. Glyceryl monoolein was heated to 43–47° C. and mixed into the solution to form a clear solution, which was mixed and cooled to room temperature.

Upon visual inspection, a clear transparent medium was observed and no nimesulide crystals were observed, suggesting that the nimesulide was only present in solution. The compositions of the Examples were also found to be physically stable, for example it was possible to keep them at 40° C. for 60 days or more.

What is claimed is:

1. A composition consisting essentially of nimesulide and 17% to 59% by weight of a glyceryl monoolein-solvent-phase, wherein the nimesulide is in the glyceryl monoolein-solvent-phase.

2. The composition of claim 1, wherein glyceryl monoolein-solvent phase has a liquid crystal structure.

3. The composition of claim 1, wherein the nimesulide comprises 0.1% to 5% by weight of the composition.

4. The composition of claim 1, further consisting essentially of a non-aqueous solvent.

5. The composition of claim 4, wherein the non-aqueous solvent is selected from the group consisting of diethylene glycol monoethyl ether (DGME) and ethanol.

6. The composition of claim 4, further consisting essentially of a gelling agent.

7. The composition of claim 6, wherein the gelling agent is hydroxypropylcellulose.

8. The composition of claim 1, further consisting essentially of a gelling agent.

9. The composition of claim 8, wherein the gelling agent is hydroxypropylcellulose.

10. A method, wherein a composition consisting essentially of nimesulide and 17% to 59% by weight of a glyceryl monoolein-solvent-phase, wherein the nimesulide is in the glyceryl monoolein-solvent phase, is administered to an animal in need of treatment for an indication selected from the group consisting of pain, inflammation and stiffness in amount effective to treat the animal.

11. The method of claim 10, wherein glyceryl monoolein-solvent phase has a liquid crystal structure.

12. The method of claim 10, wherein the nimesulide comprises 0.1% to 5% by weight of the composition.

13. The method of claim 10, further consisting essentially of a non-aqueous solvent.

14. The method of claim 13, wherein the non-aqueous solvent is selected from the group consisting of diethylene glycol monoethyl ether (DGME) and ethanol.

15. The method of claim 13, further consisting essentially of a gelling agent.

16. The method of claim 15, wherein the gelling agent is hydroxypropylcellulose.

17. The method of claim 10, wherein the composition is administered in a form selected from the group consisting of a gel, a solution, an ointment and a spray.

18. The method of claim 17, wherein the composition is administered in the form of a gel.

19. The method of claim 10, further consisting essentially of a gelling agent.

20. The method of claim 19, wherein the gelling agent is hydroxypropylcellulose.

* * * * *